United States Patent [19]

Han et al.

[11] Patent Number: 5,547,863
[45] Date of Patent: Aug. 20, 1996

[54] PRODUCTION OF FRUCTAN (LEVAN) POLYFRUCTOSE POLYMERS USING BACILLUS POLYMYXA

[75] Inventors: Youn W. Han; Margaret A. Clarke, both of New Orleans, La.

[73] Assignee: The United States of America as represented by the Secretary of the Agriculture, Washington, D.C.

[21] Appl. No.: 393,604

[22] Filed: Aug. 14, 1989

[51] Int. Cl.$^6$ .............................. C12P 19/04; C07G 3/00; C07D 413/00
[52] U.S. Cl. ........................... 435/101; 435/838; 536/4.1; 536/114
[58] Field of Search ..................... 435/101, 838, 435/252.5; 536/4.1, 114

[56] References Cited

U.S. PATENT DOCUMENTS

| | | | |
|---|---|---|---|
| 2,673,828 | 3/1954 | Koepsell | 435/193 |
| 3,879,545 | 4/1975 | Gaffar et al. | 424/92 |
| 4,329,448 | 5/1982 | Cox et al. | 536/114 |
| 4,399,221 | 8/1983 | Schneider | 435/193 |
| 4,769,254 | 9/1988 | Mays | 426/564 |

OTHER PUBLICATIONS

Murphy, D., Can. J. Chem., vol. 30, (1952), pp. 872–878.
Cooper, et al., J. Soc. Chem. Indust., vol. 58, (1939), pp. 229–231.
Hestrin, et al., Biochem. J., vol. 37, (1943), pp. 450–456.
Forsyth, et al., Biochem. J., vol. 44, (1949), pp. 455–459.
Clarke, et al., Abstract presented at the XIVth International Carbohydrate Symposium, Stockholm, Sweden, Aug. 14–19, 1988.

Primary Examiner—Douglas W. Robinson
Assistant Examiner—Pamela Webber
Attorney, Agent, or Firm—M. Howard Silverstein; John D. Fado

[57] ABSTRACT

Soil isolates, identified as strains of *Bacillus polymyxa*, NRRL B-18475 and NRRL B-18476, produce large quantities of a pure and uniform extracellular polysaccharide fructan (levan), in a sucrose medium. The levan consists entirely of fructose and the residues linked by β, 2-6 fructofuranoside linkage.

5 Claims, No Drawings

PRODUCTION OF FRUCTAN (LEVAN) POLYFRUCTOSE POLYMERS USING BACILLUS POLYMYXA

BACKGROUND OF THE INVENTION

1. Field of the Invention

This invention relates to fructan (levan) polyfructose polymers and methods for their preparation using strains of the bacteria *Bacillus polymyxa* (*B. polymyxa*). Levans are natural polymers of the sugar fructose, broadly (or generally) called fructans, in which the D-fructofuranoside monomeric units are linked by a β,2-6 bond. These polymers are found in many plants and microbial products and are useful as emulsifying and thickening agents in the food industry.

2. Description of the Prior Art

Fructans occur naturally in two general forms distinguished by the type of linkage between the fructose molecules as illustrated:

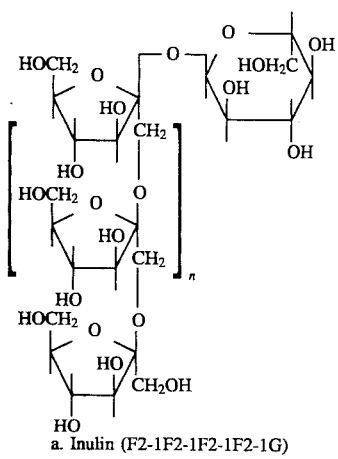

a. Inulin (F2-1F2-1F2-1F2-1G)

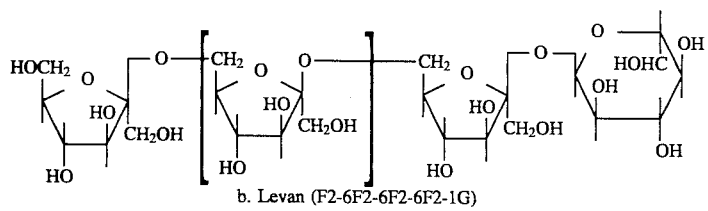

b. Levan (F2-6F2-6F2-6F2-1G)

Inulin, the form found in many plants, is formed with a backbone of β,2-1 linked fructose molecules. Levans, formed as microbial products, have a backbone of β,2-6 linked fructose molecules. Plant fructans (phleins) have shorter residues (about 100 residues) than microbial levans that contain up to 3 million residues [Pontis et al., Biochemistry of Storage Carbohydrates in Green Plants, Dey and Dixon (eds.), Ch. 5, (1985), p. 205, Academic Press, New York]. Microbial levans are produced from sucrose-based substrates by a variety of microorganisms: Acetobacters, Loewenberg, et al., Can. J. Microbiol., Vol. 3, (1957), p. 643; Achromobacter sp., Lindberg, G., Nature, Vol. 180, (1957), p. 1141; *Aerobacter aerogenes*, Srinivasan, et al., Science, Vol. 127, (1958), p. 143; *Phytobacterium vitrosum*, Belval, et al., Compt. Rend., Vol. 224, (1947), p. 847 and Vol. 226, (1948), p. 1859; *Xanthomonas pruni*, Cooper, et al., Biochem. J., Vol. 29, (1935), p. 2267; *Bacillus subtilis* [Dedonder, R., Meth. Enzymol., Vol. 8, (1966), p. 500 and Tanka, et al., J. Biochem., Vol. 85, (1979), p. 287]; *B. polymyxa* [Hestrin et al., Biochem. J., Vol. 3, (1943), p. 450]; *Aerobacter levanicum* (Hestrin, et al., Ibid.); Streptococcus sp. [Corrigen et al., Infect. Immun., Vol. 26, (1979), p. 387]; Pseudomonas [Fuchs, A., Nature, Vol. 178, (1956), p. 921]; *Corynebacterium laevaniformans* (Dias et al., Antonie Van Leewenhoeck, Vol. 28, (1962), p. 63]. Early reports on levan were obscured by incomplete description of impure products, and yields too low to consider for industrial applications. Levans (fructans) were identified by hydrolysis (acid) yielding β-fructose, and analysis agreeing with the empirical formula $(C_6H_{10}O_5)_n$.

Polysaccharide gums such as the dextrans or xanthan gums are used extensively in the food industry as stabilizers in emulsions and foams such as ice cream, whipped toppings and salad dressings, etc. (Sharma, S.C., J. Food Tech., January 1981, p. 59).

Extracellular polysaccharides produced by microorganisms offer a variety of useful and potentially low-cost industrial gums.

Conventionally, small quantities of levan have been produced by the bacterial fermentation of sucrose using strains of *Actinomyces viscosus* or *Aerobacter levanicum*. *B. polymyxa* generally produce heteropolysaccharides, comprising several different forms of polymers. Genetically engineered *Escherichia coli* (*E. coli*) have been produced that will synthesize levan, [Gay, P., et al., J. Bacteriol., Vol. 153, (1983), p. 1424]. Additionally, other methods using aerobic fermentation aimed at the production of levan [Jeanes, et al., U.S. Pat. No. 2,673,828; Gaffor, et al., U.S. Pat. No. 3,879,545; Ayerbe, et al., U.S. Pat. No. 4,399,221] as well as those described above suffer the disadvantages of low yield and contaminating or impure products. As such, there is a need in the industry for an efficient microbial method for increased levan production.

SUMMARY OF THE INVENTION

It is the object of the present invention to provide a means for the increased production of levan essentially free of contaminating polysaccharides. The levan described is aβ,2-6 linked fructofuranoside polymer produced by a strain of *B. polymyxa* isolated from soil. Surprisingly, this isolate produces levan at about three times the amount of previously known levan synthesizing microorganisms and essentially free from other contaminating polysaccharide fermentation products.

DETAILED DESCRIPTION OF THE INVENTION

EXAMPLE 1

Isolation and Identification of a Levan Producing Microorganism.

A levan producing bacterium was isolated from soil and identified as a strain of *Bacillus polymyxa*. In short, about 1 g of rotting sugarcane stalks and the adhering soil particles were added to 100 ml of basal medium and incubated at 30°

C. with constant shaking. Subsequently, one ml of growth culture was transferred to fresh media every 7–10 days. After several successive transfers, the culture was plated on the same medium solidified with agar. Bacterial colonies were separated from fungal and yeast colonies and transferred into a fresh medium and incubated until full growth. A portion of the growth medium was withdrawn and centrifuged to remove the cells and other insolubles. One and half volume of ethanol or isopropanol was added to the supernatant and the resulting precipitate collected by gently siphoning off the supernatant. The precipitates were then hydrolyzed in boiling oxalic acid (0.5%) for 30 minutes (min) and the polarity (optical rotation) of the solution determined. The samples showing negative polarization were tentatively selected as positive for levan production. Repeated enrichment, plating and product identification were continued until a pure culture of a levan producer was obtained.

Two strains of the *B. polymyxa* described above have been deposited with the Agricultural Research Service Culture Collection (NRRL), Peoria, Ill.. They have been assigned the numbers NRRL B-18475 and NRRL B-18476. The strain that produced highest yields of levan was cultivated on a defined medium, which consisted of sucrose, 80 g; peptone, 2 g; yeast extract, 2 g; $K_2HPO_4$,2 g; $(NH_4)_2SO_4$,2 g; $MgSO_4$,0.3 g; in 1 liter of water. In an alternate embodiment, sugarcane juice with no added nutrients was used as a growth medium. Isolated bacterial cells appeared as short rods with 2–10 µ length and 0.5–1.0 µ width; they occurred singularly and motile with peritrichous flagella. The cells stained Gram variable. Colonies became gummy and adhered to the agar surface, especially on sucrose media. Sporulation was rare but some subterminal spores were observed after 30 days cultivation on nutrient agar. Cells had swollen sporangia. Cells grew at temperatures ranging from 25° to 37° C. and gas and acid were formed on glucose, a characteristic of *B. polymyxa*. Additional physiological and nutritional characteristics of the isolate were similar to that of *B. polymyxa*.

EXAMPLE 2

Production of a Levan.

The isolate (*B. polymyxa*, NRRL B-18475) produced a large quantity of extracellular polysaccharides when grown on 4–16% sucrose. The levan production was noted after a few days cell growth and the level reached maximum after cell growth reached stationary phase. Routinely, at least a 5–10-day cultivation time was needed for a maximum yield. The pH of the growth medium fell from 7.0 to 4.7 due to acid production. Optimum temperature for growth and levan production was around 30° C. In a typical fermentation, the isolate produced about 3.6 g of levan in 100 ml of 15% sucrose medium in 10 days (about 50% yield on available fructose). During the same period, other bacteria known to produce levan yielded lesser amounts or did not produce at all (Table 1). The polysaccharide production was especially pronounced when the culture was gently shaken during the cultivation period. About three times more levan was produced on shake culture than still culture (Table 2). However, vigorous agitation and aeration inhibited levan production.

Levan production by the organism was dependent on the type and concentration of sugar. The highest amount of levan (57.3 g/1 wet wt. 50% moisture) was produced on the medium containing about 8% sucrose, while the yield decreased at higher or lower sucrose concentrations (Table 3). A minor amount of microbial polysaccharide (alcohol precipitate) was also produced when the organism was grown

TABLE 1

Comparative production of levan by different organisms.

| Organism | Levan[a] (g/100 ml) |
|---|---|
| *Acetobacter pasteurianus* | |
| ATCC 11142 | 0 |
| *B. polymyxa* | |
| NRRL B-68 | 0 |
| NRRL B-130 | 0 |
| NRRL B-510 | 1.2 |
| NRRL B-4317 | 1.4 |
| Isolate (NRRL B-18475) | 3.6 |
| *B. subtilis* | |
| NRRL B-447 | 1.0 |
| NRRL B-577 | 0 |
| NRRL B-644 | 0 |
| NRRL B-675 | 1.0 |
| NRRL B-744a | 1.5 |
| NRRL B-2612 | 0 |
| *Enterobacter levanicum* | |
| NRRL B-1678 | 0.7 |
| *Microbacterium laevaniformans* | |
| ATCC 15953 | 1.2 |

[a]Alcohol precipitate, air dried, (about 50% moisture), average of triplicate samples.

TABLE 2

Composition[a] of the spent fermentation broth of *B. polymyxa* grown under various cultural conditions.

| Cultivation | Levan (%) | sucrose (%) | glucose (%) | fructose (%) |
|---|---|---|---|---|
| Shake flask | 2.21 | 1.82 | 0.41 | 0.10 |
| Still flask | 0.99 | 2.12 | 0.33 | 0.07 |
| Shake flask, dark[b] | 2.12 | 1.89 | 0.42 | 0.09 |
| Fermentor[c] | 1.11 | — | — | — |
| Unfermented medium | 0 | 7.50 | 0.15 | 0.10 |

[a]Carbohydrate determined by HPLC after 10-day fermentation at 30° C.
[b]Shaken culture under dark environment.
[c]A 10-liter culture in a baffled fermentor, agitated (200 rpm) with a motor driven impellers and aerated (2 l/min) for 10 days.

TABLE 3

Effect of sugar on levan production by *B. polymyxa*

| Sugar, (%) | Levan[a] (g/l) |
|---|---|
| Control [0% (no sugar)] | 0 |
| Sucrose, 2 | 7.1 |
| Sucrose, 4 | 29.1 |
| Sucrose, 6 | 50.0 |
| Sucrose, 8 | 57.3 |
| Sucrose, 10 | 40.2 |
| Sucrose, 12 | 36.0 |
| Sucrose, 14 | 38.0 |
| Sucrose, 16 | 32.0 |
| Glucose, 6 | 0 |
| Fructose, 6 | 0 |
| Lactose, 6 | 5.1 |
| Maltose, 6 | 5.5 |
| Raffinose, 6 | 8.1 |
| Sugarcane juice[b] | 11.9 |

[a]Alcohol precipitate, air dried, (about 50% moisture), average of triplicate samples.
[b]Unfortified sugarcane juice containing about 15% sucrose.

on lactose, maltose and raffinose, but not on glucose or fructose. The isolate produced polysaccharide from sugarcane juice, but the yield was less than that obtained from the basal medium containing the same concentration of sucrose. Levan was harvested by precipitation from the culture broth by addition of ethanol or isopropanol. The yield and consistency of the product varied depending on the amount of alcohol added. The levan started to precipitate at the medium/alcohol ratio of 1:1.2 and the yield peaked at the ratio of about 1:1.5. Further increase in the ratio resulted in hardening of the levan making the fermentation product less fluid. Slightly less isopropanol was needed than ethanol to precipitate levan. Although most of the bacterial cells, unfermented sugars and other solubles remained in the aqueous alcohol phase, preremoval of microbial cells by centrifugation was desired to obtain a pure form of levan. The final product was a off-white, gummy material which could be freeze-dried or vacuum-dried. This was further purified by dialysis or ultrafiltration of a second precipitation with 75% ethanol.

EXAMPLE 3

Levan Characterization.

The levan produced by the isolate B. polymyxa consisted of about 98% fructose as revealed by HPLC of the acid hydrolysate. The product was readily soluble in water and insoluble in 75% alcohol at room temperature. In contrast to low solubility of inulin ($\beta$,2-1 linkage) the high solubility of the product may be a characteristic of $\beta$,2-6 linked levans. The product was very susceptible to hydrolysis in boiling 0.5% oxalic acid. Since the initial molecule in levan formation is sucrose, terminal glucose groups are expected to be present in levan chains. However, because of the small portion of terminal groups in their high molecular weight levan, essentially no glucose was observed on hydrolysis or on methylation analysis. On gel permeation chromatography, a 5% aqueous solution of crude levan, after dialysis through a membrane with 12,000 daltons cut-off, gave a single, sharp clean peak about $2 \times 10^6$ daltons on Sephacryl S-500. While the polymer of the present invention may have a range of molecular weights of from about $1.5 \times 10^6$ to about $2.5 \cdot 10^6$ daltons, the aforementioned peak is sharper (narrower molecular weight range) than those of the commercially available dextrans used as GPC standards. The uniformity of the product is perhaps due to the result of a long fermentation period (up to 10 days) and lack of levan-hydrolyzing activity in the levan-sucrase of the organism. Levan hydrolyzing activity is commonly found in other levan producers. The compound is stable in aqueous solution at pH 4.5 for up to 36 hr when monitored by HPLC analysis. The degree of optical rotation was determined using a polarimeter (Type AA-10, Optoelectronic Design Engineers, LTD., England) with a sodium lamp and a 100 mm sample tube. The amount of fructose in the levan hydrolysate was determined by comparing the degree of optical rotation produced by the sample and the standard fructose solution. While various samples of the polymer of the present invention may exhibit negative optical rotation $[\propto]D^{24}$ of from about $-40$ to about $-46$ depending upon the degree of branching, at optimum level of production the optical rotation $[\propto]D^{24}$ will be $-42.0$. It is non-hygroscopic, which is unusual in view of its high solubility; this advantage facilitates ease of handling and storing. Lyophilized sheets of levan have been maintained under atmospheric condition for up to six months.

Carbon-13 n.m.r. spectroscopy was performed at 100 MHz with a JEOL GX-400 instrument, at 70° C., with internal standard 1,4-dioxane ($\delta$67-40). Methylation analysis was run by the method of Hakomori, S., Biochem. (Tokyo), Vol. 55, (1964), p. 205 followed by hydrolysis with trifluoracetic acid, sodium borohydride reduction, and acetylation, in which partially methylated monomers were converted to alditol acetate. Gas liquid chromatography was performed on a Hewlett-Packard 5970, used as an inlet for mass spectrometer. Molecular weight was determined on a Sephacryl S-500 column (2.6×70 cm), using deionized water as solvent, upward flow of 2.75 ml/min. and detected by a refractive index monitor, Model R-401 (Waters Associates, Milford, Mass.).

The inulin used for infrared analysis was provided by A. French of USDA, Southern Regional Research Center, New Orleans. The $^{13}$C n.m.r. spectrum indicates that essentially all fructose molecules in the polymer are in the same conformation. In Table 4, n.m.r. peaks from the fructan isolate are compared to peaks from known inulin ($\beta$,2-1 linked) and known bacterial levan ($\beta$,2-6 linked), from Barrow et al., Eur. J. Biochem., Vol. 145, (1984), p. 173. The primary carbons (C1 and C6) are more closely grouped in inulin, and the ring carbons (C3, C4 and C5) are more closely grouped in levan, characteristic of the published differences between inulin and levan [French, A., Chemical and Physical Properties of Fructans, Proc. 1st. Int. Symp. on Fructans, July 1988, Bonn, Fed. Rep., Germany. Data clearly show the polysaccharide produced by the isolate to be of the bacterial levan type with the linkage of $\beta$,2-6 fructofuranoside. The infrared spectra of inulin and bacterial levan showed similar characteristics between them.

After methylation, analysis on GLC provided a chromatogram, wherein branch points are indicated by the presence of 3,4 dimethyl substituted fructose. Mass spectrometric data confirm the assignments and indicate the degree of branching of 12%. This observation is supported by the observation of 13% terminal groups, indicated by tetramethylated fructose residues, substituted at the 1- or 2-position (Table 5). The branches are formed by $\beta$,1-2 linkage with side chains of $\beta$,6-2 linked residues. The degree of branching in levans has been shown to range from 5–20% [Lindberg et al., Acta

TABLE 4

Assignment of peaks for chemical shifts in $^{13}$C n.m.r. spectra of inulin, levan and the fructan isolate from B. polymyxa.

| Carbon atom | 1 | 2 | 3 | 4 | 5 | 6 |
|---|---|---|---|---|---|---|
| Inulin[a] | 62.2 | 104.5 | 78.5 | 76.6 | 87.4 | 63.4 |
| Levan[a] | 61.4 | 105.1 | 77.5 | 76.6 | 81.3 | 64.6 |
| Fructan-isolate[b] | 61.4 | 105.0 | 77.8 | 76.4 | 81.1 | 64.2 |

[a]Assignment cited from Barrow, K. D., J. G. Collins, P. L. Rogers, and G. M. Smith, Eur. J. Biochem., Vol. 145 (1984), pp. 173–179.
[b]Polysaccharide isolated from B. polymyxa product, dissolved in D$_2$O at 70° C.

TABLE 5

Linkage types as indicated by methylation analysis.

| Linkage type | % |
|---|---|
| $\beta$, (2–6) linked fructose | 71 |
| Branch points (at 1, 2, 6) | 12 |
| Terminal groups (1 or 2 position) | 13 |
| Free hexose | 4 |

Chem. Scand., Vol. 27, (1973), p. 1898]. The free hexose probably resulted from material that was not dissolved during methylation. While Table 5 lists characteristics for a polymer of the present invention produced at optimum production conditions, the present invention also encompasses the following characteristics: 68% to 74% β,2-6 linked fructose, with 10% to 14% branch points and 10% to 15% terminal groups; and the polymer is non-hygroscopic but readily soluble in water.

Thus, it is evident that there has been provided in accordance with the present invention, isolates of *B. polymyxa* capable of being used in processes for the production of levan that fully satisfy the advantages described hereinabove.

We claim:

1. A biologically pure culture of *Bacillus polymyxa* selected from the group of deposits consisting of NRRL B-18475 and NRRL B-18476.

2. A method of producing a β,2-6 linked fructofuranoside polymer comprising:
   a) incubating *Bacillus polymyxa* selected from the group of deposits consisting of NRRL B-18475 and NRRL B-18476 in a media comprising one or more sugars under conditions suitable for said Bacillus to produce said polymer; and
   b) recovering said polymer.

3. A fermentation broth comprising
   a) *Bacillus polymyxa* selected from the group consisting of NRRL B-18475 and NRRL B-18476; and
   b) a sugar selected from the group consisting of sucrose, glucose, fructose, lactose, maltose and raffinose or mixtures thereof.

4. A polyfructose polymer having the properties: molecular weight of from about $1.5 \times 10^6$ to about $2.5 \times 10^6$ daltons: negative optical rotation $[\propto]D^{24}$ of from about $-40$ to about $-46$; 68%–74% β,2-6 linked fructose, with 10%–14% branch points and 10%–15% terminal groups; said polymer being non-hygroscopic and readily soluble in water.

5. The polyfructose polymer of claim 4 having the properties: a molecular weight of about $2 \times 10^6$ daltons, an optical rotation $[\propto]D^{24}$ of $-42.0$, 71% β,2-6 linked fructose with 12% branch points and 13% terminal groups.

* * * * *